(12) United States Patent
Nose et al.

(10) Patent No.: US 7,109,369 B2
(45) Date of Patent: Sep. 19, 2006

(54) MALONIC ACID MONOMETHYL DERIVATIVES AND PRODUCTION PROCESS THEREOF

(75) Inventors: Satoru Nose, Arai (JP); Kieko Sano, Himeji (JP); Takeshi Hamatani, Arai (JP)

(73) Assignee: Daicel Chemical Industries, Ltd., Sakai (JP)

( * ) Notice: Subject to any disclaimer, the term of this patent is extended or adjusted under 35 U.S.C. 154(b) by 4 days.

(21) Appl. No.: 10/976,966

(22) Filed: Nov. 1, 2004

(65) Prior Publication Data

US 2005/0124825 A1    Jun. 9, 2005

(30) Foreign Application Priority Data

Dec. 8, 2003    (JP)    ............. 2003-409350

(51) Int. Cl.
C07C 69/76    (2006.01)
(52) U.S. Cl. ....................................... 560/82
(58) Field of Classification Search ............ None
See application file for complete search history.

(56) References Cited

U.S. PATENT DOCUMENTS

| 4,588,746 A | 5/1986 | Watthey |
| 5,869,657 A | 2/1999 | Annis et al. |

FOREIGN PATENT DOCUMENTS

| JP | 5-25164 A | 2/1993 |
| WO | WO-91/05763 A1 | 5/1991 |
| WO | WO 95/29171 A1 | 11/1995 |
| WO | WO 00/10963 A1 | 3/2000 |

OTHER PUBLICATIONS

J. Org. Chem., 65, 2000, pp. 5834-5836.
J. Amer. Chem. Soc., 74, 1952 pp. 5897-5899.
J. Med. Chem.,13, 1970 pp. 820-826.
Synthesis, 6, 1987 pp. 565-566.
Takuwa et al., Chemistry Letters, vol. 33, No. 1, pp. 8-9 (2004).
Bohme et a., J. Med. Chem., vol. 46, pp. 856-867 (2003).

Primary Examiner—Paul A. Zucker
(74) Attorney, Agent, or Firm—Birch, Stewart, Kolasch & Birch, LLP

(57) ABSTRACT

A novel monomethyl malonate derivative is represented by following Formula (I):

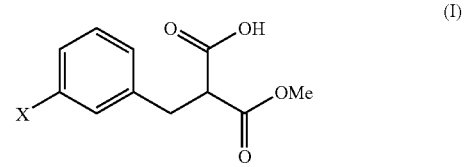

wherein X is a halogen atom; and Me is methyl group. This compound can be prepared by the steps of (A) reacting a benzyl halide derivative represented by following Formula (II):

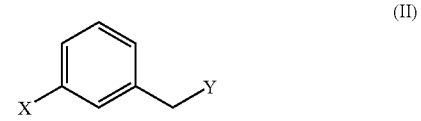

wherein X and Y may be the same as or different from each other and are each a halogen atom, with dimethyl malonate in the presence of a base to yield a dimethyl malonate derivative represented by following Formula (III):

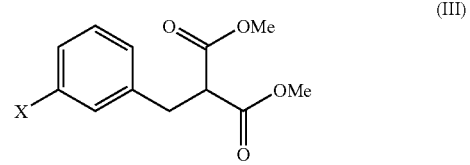

wherein X and Me have the same meanings as defined above; and (B) hydrolyzing the dimethyl malonate derivative of Formula (III). The compound is useful in the production of an indanonecarboxylic acid ester having a halogen atom on the indanone ring.

2 Claims, No Drawings

MALONIC ACID MONOMETHYL DERIVATIVES AND PRODUCTION PROCESS THEREOF

This Nonprovisional application claims priority under 35 U.S.C. §119(a) on Patent Application No(s). 2003-409350 filed in JAPAN on Dec. 8, 2003, the entire contents of which are hereby incorporated by reference.

BACKGROUND OF THE INVENTION

1. Field of the Invention

The present invention relates to novel monomethyl malonate derivatives and a production process thereof. The novel monomethyl malonate derivatives serve as precursors for indanonecarboxylic acid esters which have a halogen atom in the indanone ring and are useful as synthetic intermediates for insecticides.

2. Description of the Related Art

Indanonecarboxylic acid esters each having a halogen atom in the indanone ring are useful as synthetic intermediates for insecticides (e.g., U.S. Pat. No. 5,869,657). Certain production processes are known for the production of these indanonecarboxylic acid esters. PCT International Publication Number WO00/10963, for example, discloses a process for preparing an indanonecarboxylic acid ester by reacting a halogenated anthranilic acid derivative with sodium nitrite or methyl nitrite to yield a diazonium salt, reacting the diazonium salt with an acrylic acid derivative in the presence of a palladium-containing catalyst to yield substituted cinnamic acid and cinnamic acid ester, hydrogenating the same by the catalysis of a hydrogenating catalyst to yield a substituted arylpropionic acid, and subjecting the substituted arylpropionic acid to ring-closing reaction in the presence of a base to yield an indanonecarboxylic acid ester. This process, however, is not suitable for commercial production, since the process uses, as an intermediate, a diazonium salt which is difficult to handle safely.

PCT International Publication Number WO 95/29171 discloses a process for preparing an indanonecarboxylic acid ester by subjecting a para-substituted phenylacetyl halide to Friedel-Crafts reaction with ethylene to yield a substituted tetralone, subjecting the substituted tetralone to ring-opening reaction in the presence of a peroxycarboxylic acid to yield a substituted arylpropionic acid, esterifying the substituted arylpropionic acid, and subjecting the ester to ring-closing reaction in the presence of a base to thereby yield a substituted indanonecarboxylic acid ester. This process, however, is not suitable for commercial production from the viewpoint of safety, since the process uses a peroxide for the ring opening of the substituted tetralone.

Japanese Unexamined Patent Application Publication No. 05-25164 discloses a process for preparing an indanonecarboxylic acid ester by esterifying a substituted indanone typically with dimethyl carbonate. The publication discloses, as an example, a process for preparing methyl indanonecarboxylate by reacting 5-chloroindanone with dimethyl carbonate in the presence of sodium hydride. However, this process only achieves a yield as low as 50% or less.

Monoethyl phenylmalonate is known as a malonic acid monoester derivative (J. Org. Chem., 65, 2000, 5834; and J. Amer. Chem. Soc., 74, 1952, 5897). Diethyl benzylmalonate and diethyl 3-benzylmalonate are known as malonic acid diester derivatives (J. Med. Chem., 13, 1970, 820; and Synthesis, 6, 1987, 565). However, these documents fail to describe monomethyl 3-halobenzylmalonates and production thereof.

SUMMARY OF THE INVENTION

Accordingly, an object of the present invention is to provide a novel monomethyl malonate derivative which is useful for the production of an indanonecarboxylic acid ester having a halogen atom on the indanone ring. Another object of the present invention is to provide a process for easy and conveniently producing the monomethyl malonate derivative.

After intensive investigations on a process for industrially efficiently producing an indanonecarboxylic acid ester having a halogen atom on the indanone ring, the present inventors have found a novel monomethyl malonate derivative, which is useful as a starting material for the indanonecarboxylic acid ester, and a process for easily and conveniently producing the monomethyl malonate derivative. The present invention has been accomplished based on these findings.

Specifically, the present invention provides a monomethyl malonate derivative represented by following Formula (I):

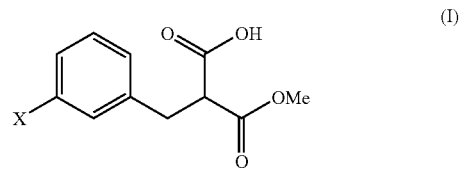

wherein X is a halogen atom; and Me is methyl group. X includes, for example, chlorine atom.

The present invention further provides a process for producing a monomethyl malonate derivative represented by following Formula (I):

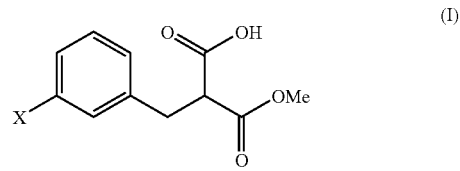

wherein X is a halogen atom; and Me is methyl group, including the steps of:

(A) reacting a benzyl halide derivative represented by following Formula (II):

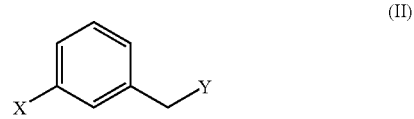

wherein X and Y may be the same as or different from each other and are each a halogen atom, with dimethyl malonate in the presence of a base to thereby yield a dimethyl malonate derivative represented by following Formula (III):

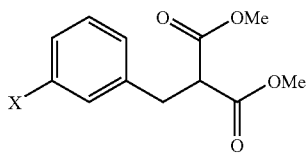

(III)

wherein X and Me have the same meanings as defined above; and (B) hydrolyzing the dimethyl malonate derivative of Formula (III). X includes, for example, chlorine atom.

Thus, the present invention provides novel monomethyl malonate derivatives which are useful for producing indanonecarboxylic acid esters useful as synthetic intermediates for insecticides. It also provides a process for easily and conveniently producing the monomethyl malonate derivatives.

The monomethyl malonate derivatives of the present invention can be used as precursors for indanonecarboxylic acid esters each having a halogen atom on the indanone ring. Such indanonecarboxylic acid esters are useful as intermediates for insecticides.

Further objects, features and advantages of the present invention will become apparent from the following description of the preferred embodiments.

DESCRIPTION OF THE PREFERRED EMBODIMENTS

The substituent X in the monomethyl malonate derivative of Formula (I) represents a halogen atom. Examples of the halogen atom are fluorine, chlorine, bromine and iodine atoms, of which chlorine atom is preferred.

A typified example of the monomethyl malonate derivative is 3-(3-chlorophenyl)-2-methoxycarbonylpropionic acid.

The monomethyl malonate derivative of Formula (I) can be produced, for example, by the steps of (A) reacting a benzyl halide derivative of Formula (II) with dimethyl malonate in the presence of a base to yield a dimethyl malonate derivative of Formula (III), and (B) hydrolyzing the dimethyl malonate derivative of Formula (III) to thereby yield the monomethyl malonate derivative of Formula (I).

In Step (A), X and Y in the benzyl halide derivative of Formula (II) may be the same as or different from each other and are each a halogen atom. The halogen atom in X is defined in the same manner as above. Examples of the halogen atom in Y are the same as those in X. Preferred examples of the halogen atom in Y are chlorine, bromine and iodine atoms, of which chlorine atom is typically preferred.

Examples of the base are carbonates including alkali metal carbonates such as potassium hydrogen carbonate, sodium hydrogen carbonate, potassium carbonate and sodium carbonate; alkali metal hydroxides such as sodium hydroxide and potassium hydroxide; alkaline earth metal hydroxides such as calcium hydroxide and magnesium hydroxide; phosphates including alkali metal phosphates such as sodium dihydrogen phosphate and potassium dihydrogen phosphate; carboxylates including alkali metal carboxylates such as sodium acetate and potassium acetate; organic bases such as triethylamine and pyridine; metal alkoxides including alkali metal alkoxides such as sodium methoxide and sodium ethoxide; and metal hydrides such as sodium hydride. Each of these bases can be used alone or in combination. Preferred examples of the base are alkali metal hydroxides.

In Step (A), the amount of dimethyl malonate is, for example, about 0.1 to about 1000 moles, preferably about 1.1 to 100 moles and more preferably about 2 to about 10 moles, per 1 mole of the benzyl halide derivative of Formula (II). Dimethyl malonate is generally used in excess, so as to suppress the formation of a by-product formed as a result of reaction between 2 moles of the benzyl halide derivative and 1 mole of dimethyl malonate. Unreacted dimethyl malonate may be recovered and reused after the completion of reaction. The amount of the base is generally about 0.01 to about 100 gram equivalents, preferably about 0.1 to about 10 gram equivalents, more preferably about 0.25 to 4 gram equivalents, and further preferably about 0.9 to about 1.5 gram equivalents, per 1 mole of the benzyl halide derivative.

The reaction may be carried out in the presence of a reaction auxiliary. Examples of the reaction auxiliary are alkali metal halides such as sodium bromide, potassium bromide, sodium iodide and potassium iodide; crown ethers such as 12-crown-4,15-crown-5,18-crown-6; and phase-transfer catalysts such as quaternary alkyls or aryl-substituted ammonium.

The reaction is carried out in the presence of, or in the absence of, a solvent. The solvent is not specifically limited as long as it is inert to the reaction components and can be separated from the product. Examples of the solvent are organic solvents and water. Such organic solvents include, for example, ketones such as acetone and ethyl methyl ketone; ethers such as tetrahydrofuran and dioxane; nitriles such as acetonitrile; sulfoxides such as dimethyl sulfoxide; sulfolanes such as sulfolane; esters such as ethyl acetate; amides such as dimethylformamide; alcohols such as methanol, ethanol and t-butanol; aliphatic or alicyclic hydrocarbons such as pentane, hexane and petroleum ether; aromatic hydrocarbons such as benzene, toluene and xylenes; halogen-containing compounds such as methylene chloride, chloroform, bromoform, chlorobenzene and bromobenzene; and high-boiling solvents such as poly(ethylene glycol)s and silicone oil. Each of these solvents can be used alone or in combination. The amount of the solvent, if used, is not specifically limited as long as the reaction components can be dissolved or sufficiently dispersed in the solvent, and the upper limit thereof may be determined depending on economical factors.

The reaction temperature is not specifically limited, as long as it is equal to or higher than the melting point of the system, and stands at, for example, from about −30° C. to about 300° C. and preferably from about −10° C. to about 200° C. The reaction efficiently proceeds even under mild conditions of around room temperature (5° C. to 40° C.). The reaction is typically preferably carried out at 20° C. to 30° C.

The reaction may be carried out under ordinary pressure, under reduced pressure or under a pressure (under a load) and is generally carried out under ordinary pressure. The reaction can be conducted according to a procedure such as batch, semi-batch or continuous procedure.

The malonic acid dimethyl derivative of Formula (III) produced by Step (A) may be isolated from the reaction mixture, but the reaction mixture containing the product can be used as a raw material for Step (B), as intact or after concentration. The product can be isolated, for example, by a separation means such as filtration, concentration, distillation, extraction, crystallization, recrystallization or column chromatography.

The amount of water for use in the hydrolysis reaction in Step (B) can be set according typically to type of the malonic acid dimethyl derivative, reaction mode and reaction rate and is, for example, from about 0.1 to about 1000000 moles, preferably from about 0.5 to about 1000 moles, more preferably from about 0.8 to 300 moles and typically preferably from about 150 to 250 moles per 1 mole of the dimethyl malonate derivative.

A reaction auxiliary such as an acid or a base may be used in the hydrolysis reaction for accelerating the reaction. Examples of the acid are inorganic acids, organic acids and solid acids. The inorganic acids include, for example, sulfuric acid, hydrochloric acid, phosphoric acid and nitric acid. The organic acids include, for example, carboxylic acids including $C_1$–$C_{10}$ saturated or unsaturated mono- or polycarboxylic acids such as acetic acid and propionic acid; sulfonic acids including $C_1$–$C_6$ alkane-sulfonic acids such as methanesulfonic acid and ethanesulfonic acid, and aromatic sulfonic acids such as benzenesulfonic acid and p-toluenesulfonic acid; and halogenated organic acids including halogenated carboxylic acids such as trifluoroacetic acid, and halogenated alkanesulfonic acids such as trifluoromethanesulfonic acid. The solid acids include, for example, sulfates such as calcium sulfate; metal oxides such as $SiO_2$ and $Al_2O_3$; zeolite such as Y-type, X-type or A-type zeolite having acidic OH; and ion-exchange resins such as H-type cation-exchange resins. Examples of the base are those exemplified as the base in Step (A). Among such resins, preferred are alkali metal hydroxides. Each of these reaction auxiliaries can be used alone or in combination.

The amount of the reaction auxiliary is not specifically limited and is, for example, from about 0.01 to about 5 moles, preferably from about 0.1 to about 2 moles and further preferably from about 0.8 to 1.2 moles per 1 mole of the dimethyl malonate derivative. The reaction can be accelerated typically by heating, if the reaction auxiliary is not used.

The reaction is carried out in the presence of, or in the absence of, a solvent. Example of the solvent are the organic solvents exemplified as the solvent in Step (A). Each of these solvents can be used alone or in combination. The solvent herein is preferably an alcohol, of which methanol is typically preferred for avoiding a halogen-exchange reaction.

The reaction temperature is not specifically limited, as long as it is equal to or higher than the melting point and is equal to or lower than the boiling point of the system, and is, for example, from about −30° C. to about 300° C. and preferably from about −10° C. to about 200° C. The reaction efficiently proceeds even under mild conditions of around room temperature (5° C. to 40° C.). The reaction is typically preferably carried out at about 20° C. to about 30° C.

The reaction may be carried out under ordinary pressure, under reduced pressure or under a pressure (under a load) and is generally carried out under ordinary pressure. The reaction can be conducted according to a procedure such as batch, semi-batch or continuous procedure.

According to the above-mentioned process, the benzyl halide derivative of Formula (II) reacts with dimethylmalonate to yield the dimethyl malonate derivative of Formula (III), and the dimethylmalonate derivative of Formula (III) undergoes hydrolysis to yield the monomethyl malonate derivative of Formula (I). The reaction product after the completion of reaction can be separated and purified by a separation means such as filtration, concentration, distillation, extraction, ion exchange, electrodialysis, crystallization, recrystallization, adsorption, membrane separation, centrifugal separation or column chromatography, or a combination of these means.

The monomethyl malonate derivative of Formula (I) according to the present invention can easily yield an indanonecarboxylic acid ester having a halogen atom on the indanone ring according to the following reaction formula:

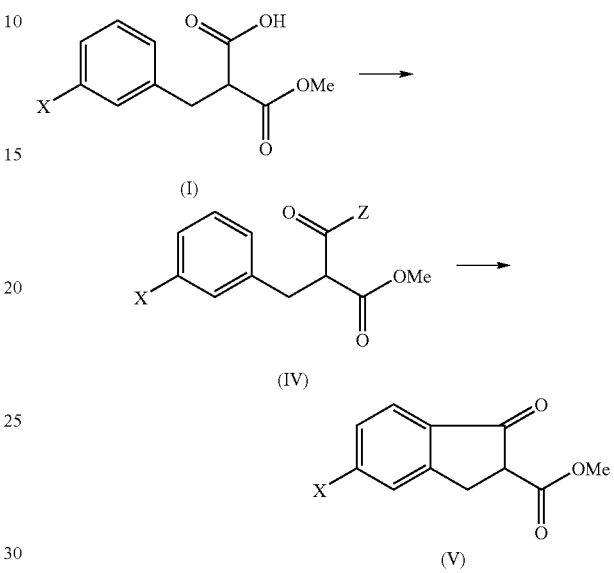

wherein X and Me have the same meanings as defined above; and Z is a halogen atom. The resulting indanonecarboxylic ester is useful as an synthetic intermediate for insecticides.

Specifically, the indanone carboxylic acid ester having a halogen atom on the indanone ring can be prepared by reacting the monomethyl malonate derivative of Formula (I) with a halogenating agent (halogenation reaction) to yield an acid halide derivative of Formula (IV), and cyclizing the acid halide derivative in the presence of a catalyst (cyclization reaction) Examples of the halogen atom in Z are fluorine, chlorine, bromine and iodine atoms.

Examples of the halogenating agent are fluorinating agents such as potassium hydrogen fluoride and potassium fluoride; chlorinating agents such as thionyl chloride, oxalyl chloride, phosphorus pentachloride and phosphorus oxychloride; brominating agents such as thionyl bromide, phosphorus tribromide, phosphorus pentabromide and phosphorus oxybromide; and iodinating agents such as phosphorus triiodide. The substituent Z in Formula (IV) is a halogen atom corresponding to the halogenating agent used. The halogenating agent is used in large excess to the monomethyl malonate derivative in a reaction in the absence of a solvent. The amount of the halogenating agent is, for example, equimolar or more and preferably 1 to 4 times by mole per 1 mole of the monomethyl malonate derivative in a reaction in the presence of a solvent.

The halogenation reaction may be carried out in the presence of a reaction auxiliary. Examples of the reaction auxiliary are zinc chloride, pyridine, iodine, triethylamine, dimethylformamide and hexamethylphosphoramide (HMPA).

The halogenation reaction is carried out in the presence of, or in the absence of, a solvent. The solvent is not specifically limited, as long as it is inert to the reaction components and can be separated from the product. Examples of the solvent are ethers such as tetrahydrofuran and dioxane; sulfoxides such as dimethyl sulfoxide; amides such as dimethylformamide; aliphatic or alicyclic hydrocarbons such as pentane, hexane and petroleum ether; aromatic hydrocarbons such as benzene, toluene and xylenes; and halogen-containing compounds such as methylene chloride, chloroform, bromoform, chlorobenzene and bromobenzene. Each of these solvents can be used alone or in combination. The amount of the solvent, if used, is not specifically limited, as long as the reaction components can be dissolved or sufficiently dispersed in the solvent, and the upper limit thereof may be determined depending on economical factors.

The reaction temperature is not specifically limited, as long as it is equal to or higher than the melting point and equal to or lower than the boiling point of the system, and is, for example, from about −30° C. to about 300° C., preferably from about −10° C. to about 200° C., and more preferably from about 10° C. to about 100° C. The reaction may be carried out under ordinary pressure, under reduced pressure or under a pressure (under a load) and is generally carried out under ordinary pressure. The reaction is conducted according to a procedure such as batch, semi-batch or continuous procedure. The reaction product can be separated and purified typically by the above-exemplified separation means. The reaction mixture may be subjected to a subsequent reaction as intact or after concentration, without isolating the reaction product.

Examples of the catalyst for use in cyclization of the acid halide derivative of Formula (IV) are Lewis acid catalysts that can be generally used for Friedel-Crafts reaction, such as anhydrous aluminum chloride, anhydrous aluminum bromide, anhydrous iron chloride, titanium tetrachloride, tin tetrachloride (stannic chloride), zinc chloride, boron trifluoride diethyl ether complex, anhydrous boron trioxide and concentrated sulfuric acid. Among them, anhydrous aluminum chloride is preferred. The amount of the catalyst is, for example, from about 1 to about 50 moles and preferably from about 2 to about 10 moles, per 1 mole of the acid halide derivative.

The cyclization reaction is carried out in the presence of, or in the absence of, a solvent. The solvent is not specifically limited, as long as it is inert to the reaction components and can be separated from the reaction product. Examples of the solvent are solvents generally used in Friedel-Crafts reaction, such as methylene chloride, chloroform, 1,2-dichloroethane, carbon tetrachloride, bromoform, chlorobenzene, nitromethane, nitrobenzene and carbon disulfide. Each of these solvents can be used alone or in combination. The amount of the solvent, if used, is not specifically limited, as long as the components can be dissolved or sufficiently dispersed in the solvent, and the upper limit thereof is determined according to economical factors.

The reaction temperature is not specifically limited, as long as it is equal to or higher than the melting point and equal to or lower than the boiling point of the system under the reaction conditions, and is, for example, from about −30° C. to about 300° C., and preferably from about −10° C. to about 100° C. The cyclization reaction may be carried out under ordinary pressure, under reduced pressure or under a pressure (under a load) and is generally carried out under ordinary pressure. The reaction can be conducted according to a procedure such as batch, semi-batch or continuous procedure.

The reaction yields a corresponding indanonecarboxylic acid ester represented by Formula (V) having a halogen atom on the indanone ring. The reaction product can be separated and purified typically by the above-mentioned separation means.

The present invention will be illustrated in further detail with reference to several examples below, which are not intended to limit the scope of the invention. Products in the examples were quantitatively analyzed by high-performance liquid chromatography. NMR spectra were measured by $^1$H-NMR at 270 MHz using JNM-EX270 (a product of JEOL Ltd.) with tetramethylsilane (TMS) as internal standard.

EXAMPLE 1

Preparation of 3-(3-chlorophenyl)-2-methoxycarbonylpropionic acid

[Step A: Preparation of dimethyl 3-chlorobenzylmalonate]

Aliquots of 6.6 g of m-chlorobenzyl chloride and 27.6 g of dimethyl malonate were dissolved in 41.8 g of dimethylacetamide, followed by mixing with 2.5 g of sodium hydroxide. The mixture was stirred at room temperature for 6 hours, was cooled to 5° C. or below, and was adjusted to pH 3.5 with 1.7 percent by weight hydrochloric acid. After adding 36.0 g of water, the product was extracted with 37.0 g of toluene, and the toluene layer was washed with two portions of 36.0 g of water. Toluene and unreacted dimethyl malonate were removed under reduced pressure, to yield 9.7 g of a concentrated residue. A total of 96 percent by weight of the residue was dimethyl 3-chlorobenzylmalonate (yield: 9.3 g, 95%).

[Step B: Preparation of 3-(3-chlorophenyl)-2-methoxycarbonylpropionic acid]

A total of 9.5 g of the residue containing dimethyl 3-chlorobenzylmalonate prepared in Step A was dissolved in 118.6 g of methanol, and 148.0 g of a 1 percent by weight aqueous solution of sodium hydroxide was added dropwise thereto. The mixture was stirred at room temperature for 3 hours, was cooled to 5° C. or below and was adjusted to pH 2.5 with 1.7 percent by weight hydrochloric acid. The product was extracted with three portions of 102.3 g of toluene, and toluene was removed under reduced pressure to yield 8.7 g of a concentrated residue. A total of 95 percent by weight of the residue was 3-(3-chlorophenyl)-2-methoxycarbonylpropionic acid (yield: 8.3 g, 92%).

[Spectral data of 3-(3-chlorophenyl)-2-methoxycarbonylpropionic acid]

$^1$H-NMR (CDCl$_3$) ppm: 3.21 (d, 2H, ClC$_6$H$_4$—CH$_2$—CH), 3.70 (t, 1H, ClC$_6$H$_4$—CH$_2$—CH), 3.74 (s, 3H, —COOCH$_3$), 7.07–7.26 (m, 4H, ClC$_6$H$_4$—)

REFERENTIAL EXAMPLE 1

Preparation of methyl 2-chloroformyl-3-(3-chlorophenyl)-propionate

A total of 8.0 g of the residue containing 3-(3-chlorophenyl)-2-methoxycarbonylpropionic acid prepared in Step B of Example 1 was dissolved in 32.8 g of 1,2-dichloroethane under nitrogen atmosphere, and 11.8 g of thionyl chloride and 0.05 g of dimethylformamide were added thereto, followed by stirring at 40° C. for 7 hours. The resulting mixture was concentrated under reduced pressure to remove 1,2-dichloroethane and unreacted thionyl chloride to thereby yield 7.98 g of methyl 2-chloroformyl-3-(3-chlorophenyl)-propionate.

[Spectral data of methyl 2-chloroformyl-3-(3-chlorophenyl)-propionate]
$^1$H-NMR (CDCl$_3$) ppm: 3.27 (d, 2H, ClC$_6$H$_4$—CH$_2$—CH), 3.78 (s, 3H, —COOCH$_3$), 4.07 (t, 1H, ClC$_6$H$_4$—CH$_2$—CH), 7.07–7.26 (m, 4H, ClC$_6$H$_4$—)

REFERENTIAL EXAMPLE 2

Preparation of methyl 5-chloro-1-oxo-2,3-dihydroindene-2-carboxylate(=5-chloro-2-methoxycarbonylindan-1-one)

Under nitrogen atmosphere, 9.0 g of anhydrous aluminum chloride and 151.3 g of 1, 2-dichloroethane were stirred to yield a suspension, and the suspension was cooled to 0° C. A mixture of 7.98 g of methyl 2-chloroformyl-3-(3-chlorophenyl)-propionate prepared in Referential Example 1 and 151.3 g of 1,2-dichloroethane was added dropwise to the suspension while maintaining the temperature at 5° C. or below, followed by stirring under the same condition for 2 hours. The reaction mixture was added dropwise to 53.6 g of 1.7 percent by weight hydrochloric acid cooled to 5° C. or below, followed by stirring under the same condition for 1 hour. After separating the mixture into a 1,2-dichloroethane layer and an aqueous layer, the product in the aqueous layer was extracted with 15.1 g of 1,2-dichloroethane. This procedure was repeated a total of two times. The resulting 1,2-dichloroethane layers obtained by these procedures were collected and were washed with 33.0 g of water, followed by removal of 1,2-dichloroethane under reduced pressure. The concentrated residue was purified by silica gel column chromatography [mobile phase: hexane/ethyl acetate=4/1 (by volume)] to yield 5.21 g of methyl 5-chloro-1-oxo-2,3-dihydroindene-2-carboxylate as a beige solid in a yield of 70% on the basis of 3-(3-chlorophenyl)-2-methoxycarbonylpropionic acid.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing a monomethyl malonate derivative represented by following Formula (I):

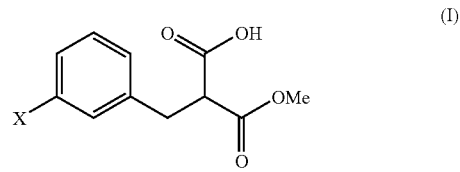

wherein X is a halogen atom; and Me is a methyl group, comprising the steps of:
(A) reacting a benzyl halide derivative represented by following Formula (II):

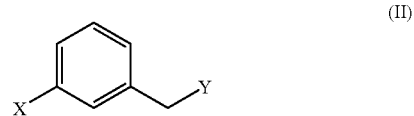

wherein X and Y may be the same as or different from each other and are each a halogen atom, with dimethyl malonate in the presence of alkali metal hydroxide to thereby yield a dimethyl malonate derivative represented by following Formula (III):

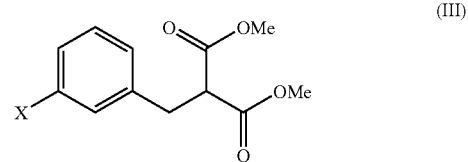

wherein X and Me have the same meanings as defined above; and
(B) hydrolyzing the dimethyl malonate derivative represented by Formula (III).

2. The process according to claim 1, wherein X is a chlorine atom.

* * * * *